(12) United States Patent
O'Brien (10) Patent No.: US 8,901,365 B2
(45) Date of Patent: Dec. 2, 2014

(54) CATALYTIC WITTIG AND MITSUNOBU REACTIONS

(75) Inventor: Christopher J. O'Brien, Arlington, TX (US)

(73) Assignee: Board of Regents, The University of Texas System, Austin, TX (US)

(*) Notice: Subject to any disclaimer, the term of this patent is extended or adjusted under 35 U.S.C. 154(b) by 32 days.

(21) Appl. No.: 13/263,224

(22) PCT Filed: Apr. 6, 2010

(86) PCT No.: PCT/US2010/030112
§ 371 (c)(1),
(2), (4) Date: Oct. 6, 2011

(87) PCT Pub. No.: WO2010/118042
PCT Pub. Date: Oct. 14, 2010

(65) Prior Publication Data
US 2012/0029211 A1 Feb. 2, 2012

Related U.S. Application Data

(60) Provisional application No. 61/167,101, filed on Apr. 6, 2009.

(51) Int. Cl.
| | | |
|---|---|---|
| *C07C 1/00* | (2006.01) | |
| *C07F 9/50* | (2006.01) | |
| *C07C 17/263* | (2006.01) | |
| *C07C 253/30* | (2006.01) | |
| *C07C 1/34* | (2006.01) | |
| *C07C 201/12* | (2006.01) | |
| *C07D 333/24* | (2006.01) | |
| *C07C 67/343* | (2006.01) | |
| *C07F 9/6568* | (2006.01) | |
| *C07C 45/68* | (2006.01) | |

(52) U.S. Cl.
CPC . *C07C 1/34* (2013.01); *C07F 9/509* (2013.01); *C07C 17/2635* (2013.01); *C07C 253/30* (2013.01); *C07C 2101/14* (2013.01); *C07C 201/12* (2013.01); *C07D 333/24* (2013.01); *C07B 2200/09* (2013.01); *C07C 67/343* (2013.01); *C07F 9/65683* (2013.01); *C07C 45/68* (2013.01)
USPC ........................................................ 585/638

(58) Field of Classification Search
CPC .................................................. C07C 17/2635
USPC .................... 549/74, 79; 560/104, 20, 211, 8; 558/401, 430, 462; 570/144; 585/640
See application file for complete search history.

(56) References Cited

U.S. PATENT DOCUMENTS

| 4,751,307 A | 6/1988 | White |
|---|---|---|
| 5,292,973 A | 3/1994 | Fukumoto et al. |
| 5,481,040 A | 1/1996 | Fukumoto et al. |

FOREIGN PATENT DOCUMENTS

JP 01259010 10/1989

OTHER PUBLICATIONS

Mundy, B.P., et al. "Name Reactions and Reagents in Organic Synthesis." © 1988, John Wiley & Sons, Wiley-Interscience Publication, pp. 226-227.*
Kuhn, F.E., et al. "Catalytic Aldehyde Olefinations." Mini-Reviews in Organic Chemistry. (2004), I, pp. 55-64.*
McKinstry, L., et al. "On the Asymmetric Rh(I) Catalyzed [4+2] Cycloisomerization Reaction. Electronic and Torsional Ligand Control of Absolute Stereoselection." Tetrahedron. (1994), vol. 50, No. 21, pp. 6145-6154.*
Li, C-Y., et al. "Enantioselective synthesis of allenic esters via an ylide route." Chem. Commun. (2006), pp. 2980-2982.*
Crepy, K.V.L., et al. "New P-Chirogenic Phosphine Ligands and Their Use in Catalytic Asymmetric Reactions." Top Curr Chem. (2003), vol. 229, pp. 1-40, Available at: < http://books.google.com/books?id=kzKr57QoDmsC&pg=PA10&lpg=PA10 &dq=LiAlH4+reducing+agent+%22phosphine+oxide%22 &source=bl&ots=7PhM9leGsH
&sig=U2ZAf5YJsf4oirfHGL5iMxN9wns&hl=en&sa=X&ei.*
Organic Chemistry Portal. "Wittig Reaction." (c) Feb. 15, 2008. Available from: < http://web.archive.org/web/20080215104421/ http://www.organic-chemistry.org/namedreactions/wittig-reaction. shtm >.*
IUPAC Gold Book. "Allene." (c) 2013. Available from: < http://goldbook.iupac.org/A00238.html >.*
IUPAC Gold Book. "Alkene." © 2013. Available from: < http://goldbook.iupac.org/A00224-plain.html >.*
Marsden, Stephen P. "The Wittig reaction cleans up", Nature Chemistry, vol. 1 (2009).
Kuhn et al. "Catalytic Aldehyde Olefinations", Mini-Reviews in Organic Chemistry, 1(1) (2004).
O'Brien et al. "Recycling the Waste: The Development of a Catalytic Wittig Reaction", Angew. Chem. Int. Ed., 48:6836-6839 (2009).
Minge et al. "Synthetic Pathways to Hydrogen-Rich Polysilylated Arenes from Trialkoxysilanes and Other Precursors", Organometallics, 21:680-684 (2002).
Awerbouch et al. "8-Phosphabicyclo[3.2.1]Octanes-II: The Synthesis and Stereochemistry of 8-Phosphabicyclo [3.2.1]Oct-6-Enes", Tetrahedron, 31:33-43 (1975).
Krech et al. "Cis-1-phosphabicyclo[3.3.0]octan", Z. Anorg. Allg. Chem., 629:1475-1476 (2003) Abstract.

* cited by examiner

*Primary Examiner* — Noble Jarrell
*Assistant Examiner* — John S Kenyon
(74) *Attorney, Agent, or Firm* — Parks IP Law LLC; Collen A. Beard, Esq.

(57) ABSTRACT

A catalytic Wittig method utilizing a phosphine including the steps of providing a phosphine oxide precatalyst and reducing the phosphine oxide precatalyst to produce the phosphine; forming a phosphonium ylide precursor from the phosphine and a reactant; generating a phosphonium ylide from the phosphonium ylide precursor; reacting the phosphonium ylide precursor with the aldehyde, ketone, or ester to form the olefin and the phosphine oxide which then reenters the cycle. The invention is also directed to a Mitsunobu reaction catalytic in phosphine.

23 Claims, 5 Drawing Sheets

CATALYTIC WITTIG AND MITSUNOBU REACTIONS

CROSS REFERENCE TO RELATED APPLICATION

This application claims priority to U.S. Provisional Application Ser. No. 61/167,101 filed on Apr. 6, 2009.

BACKGROUND OF THE INVENTION

The formation of carbon-carbon double bonds represents one of the pillars on which modern synthetic chemistry is based because the production of many natural products and drugs necessitate their assembly. Consequently numerous processes for the construction of carbon-carbon double bonds have been developed. Besides direct elimination, there are currently four reliable methodologies for the routine formation of alkenes: the Wittig, Peterson, and Kocienski-Julia olefination reactions, as well as metathesis. Currently only metathesis is catalytic and even this is limited in requiring alkene starting materials, with high loading of a suitably ligated transition metal catalyst, usually Ru or Mo, often required and, in the case of ring closing metathesis, high dilution. The use of transition metals may lead to complications in that any transition metal must be removed or substantially reduced for any products intended to be used as active pharmaceutical agents, for example.

In addition, environmental concerns increasingly influence decision making insofar as chemical synthetic route selection, which is impacted by the waste and energy consumption profile of a particular process. The Wittig reaction, for example, which is the most widely employed olefination process, comes at a cost—the stoichiometric formation of phosphine oxide byproduct.

Therefore the development of new eco-friendly catalytic methodology, which either limits the generation of waste or downgrades the waste produced, for example from toxic to harmful, would be highly desirable. The successful design and implementation of organocatalytic processes offers the possibility of lessening the environmental footprint that chemical industries have on their surrounding ecology. Therefore, an organocatalytic methodology that yields the possibility to construct olefins selectively would represent an important advance.

Of the three stoichiometric olefination processes mentioned above, the only one that may offer the realistic possibility to transition from a stoichiometric to a catalytic process, coupled with the selective formation of either E or Z alkenes, is the Wittig reaction. The Wittig reaction was discovered in 1953 by Georg Wittig and involves the treatment of an aldehyde or ketone with a phosphonium ylide, which yields an alkene concomitant with the generation of a phosphine oxide. Wittig's pioneering studies in this area resulted in his receipt of the 1979 Noble Prize for Chemistry. Since its discovery, the Wittig reaction has been used extensively, demonstrated by its inclusion in numerous natural product syntheses and undergraduate laboratory courses and teaching texts.

Figure 1:
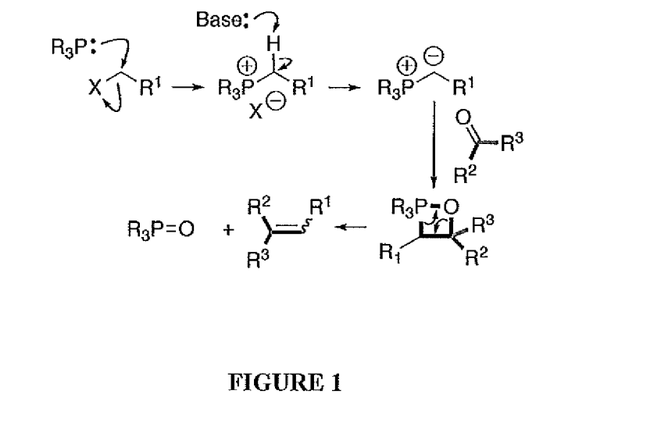
FIG. 1 illustrates a mechanism for the Wittig reaction.
Figure 2:
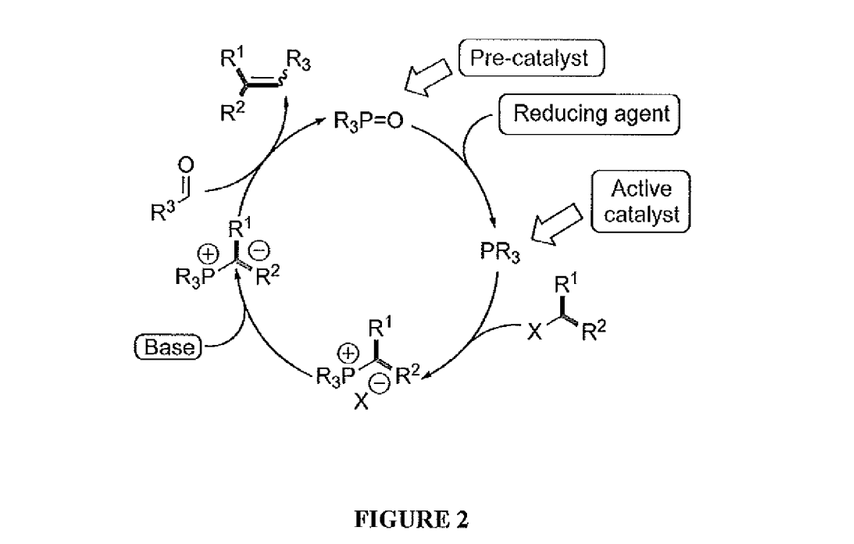
FIG. 2 illustrates the cycle for a proposed catalytic Wittig reaction.

FIG. 1 illustrates a prior art textbook illustration for the Wittig reaction. The accepted mechanism involves the attack of a phosphonium ylide on an aldehyde or ketone, yielding an oxaphosphetane intermediate. Formation of the oxaphosphetane can occur through a direct [2+2] cyclo-addition reaction between the phosphonium ylide and the carbonyl compound. Alternatively it has been proposed that a betaine intermediate is first formed. The oxaphosphetane intermediate subsequently collapses via a retro-[2+2] cyclo-addition reaction to produce the desired alkene concomitant with phosphine oxide byproduct. Further discussion of the Wittig reaction can be found in O'Brien et al., Angew. Chem. Int. Ed. 2009, 48, 6836-6839 and references cited therein.

Although there has been significant work directed towards the development of the Wittig reaction, significant problems still persist and remain to be addressed. For one thing, the process is stoichiometric and for another, complete removal of the phosphine oxide byproduct is at best time consuming or is impossible. In some cases also, Wittig reactions give diastereomeric mixtures with ensuing purification issues. A catalytic protocol would reduce the amount of the phosphine oxide byproduct. The lack of a catalytic protocol also removes from serious consideration the possibility to control the olefination by alteration of the phosphine's structure. This is unfortunate, as the phosphine's structure has been shown to have a substantial impact on the stereochemical outcome of the reaction, and therefore a carefully designed phosphine may yield a selective process.

That said, the barriers to the development of a catalytic Wittig reaction are formidable, and the successful construction of a catalytic process relies on the completion of four steps: A) formation of the phosphonium ylide precursor, typically a phosphonium salt; B) generation of the phosphonium ylide, normally by deprotonation; C) olefination with concomitant generation of phosphine oxide; and D) reduction of the phosphine oxide byproduct producing phosphine to reenter the catalytic cycle. The most daunting of the aforementioned processes is step D—the required chemoselective reduction of the phosphine oxide byproduct to a phosphine in the presence of either an aldehyde or ketone starting material and alkene product.

One could ameliorate this problem of chemoselective reduction by the replacement of phosphorus with arsenic, tellurium, or antimony, as their corresponding oxides, owing to bond strength, are appreciably easier to reduce. In fact, such an approach has led to the successful development of catalytic Wittig-type processes employing arsines and tellurides (For a review on catalytic aldehyde olefinations see F. E. Kuhn, A. M. Santos, Mini-Rev. Org. Chem. 2004, 1, 55-64). Unfortunately, significant drawbacks to the broad adoption of the aforementioned methodologies are the intrinsic high toxicity and carcinogenicity of arsenic, tellurium, and antimony compounds; environmental contamination particularly of groundwater would be one concern if these reactions were performed on a large scale. Importantly, the catalytic use of phosphine would not suffer from these issues; therefore a Wittig reaction catalytic in phosphine would find wider employment. Furthermore, this would marry the power of the Wittig olefination protocol to the synthetic benefits of a catalytic reaction without the poisoning issues that can plague transition metal catalyzed processes.

This aforementioned reduction of phosphine oxide to phosphine is pivotal to the successful development of any catalytic Wittig process; therefore the available methodology to effect this reduction merits a detailed discussion. To date the most successful class of reagents for the reduction of phosphine oxides to phosphines is silanes. Other methodologies exist but none have the scope and reliability of silanes. Fritzsche and co-workers first reported the reduction of phosphine oxides with silanes in 1964 (Fritzsche, H. et al., Reduction of organic compounds of pentavalent phosphorus to phosphines. I. Reduction of tertiary phosphine oxides to tertiary phosphines with silanes. Chem. Ber. 1964, 97, 1988-1993; Fritzsche, H. et al., Reduction of organic compounds with pentavalent phosphorus to phosphines. Reduction of tertiary phosphine oxides to tertiary phosphines with trichlorosilane. *Chem. Ber.* 1965, 98, 171-174; Fritzsche, H. et al., Reduction of organic compounds of pentavalent phosphorus to phosphines. III. Preparation of primary and secondary phosphines with silanes. *Chem. Ber.* 1965, 98, 1681-1687).

These publications are a thorough evaluation of silane reducing agents, and four successful reducing agents emerged: phenylsilane, diphenylsilane, triphenylsilane, and trichlorosilane. Since Fritzsche's work, phenylsilane and trichlorosilane have emerged as the most widely utilized with the latter, often coupled with an amine base, the most employed.

The mechanism of reduction is dependent on the silane, and in the case of trichlorosilane in the presence of an amine often leads to inversion of the phosphorus center, while with phenylsilane reduction is achieved with retention.

Efforts towards the development of catalytic processes in the Wittig reaction have primarily focused on two main areas: 1) catalytic generation of the phosphonium ylide or 2) substitution of phosphorous by arsenic due to the reduction of the arsenic-oxygen bond being more easily achieved than the analogous phosphorus-oxygen bond. However, neither represents a true catalytic Wittig reaction, as this would necessitate the catalytic use of phosphine. Indeed, the only documented use of catalytic phosphine was disclosed for the related aza-Wittig reaction; however, the reduction protocol, an isocyanate, cannot be utilized in the parent reaction. Therefore, the development of a catalytic Wittig reaction where the phosphine is the catalytic species has not before been achieved.

Figure 7:
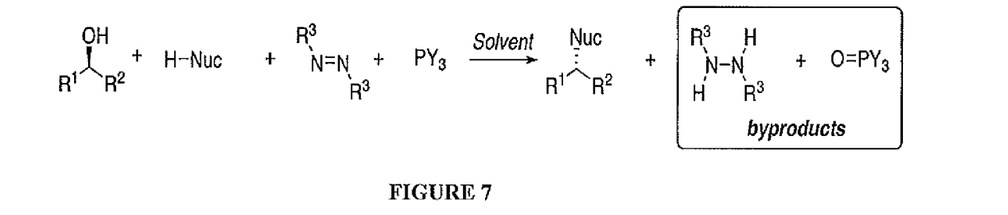
FIG. 7 illustrates the Mitsunobu reaction.

The Mitsunobu reaction also utilizes a phosphine, in the conversion of primary and secondary alcohols to esters, phenyl ethers, thioethers, and various other compounds. The general mechanism is shown in FIG. 7. Discovered in 1967 by Professor Oyo Mitsunobu, the reaction is extensively employed in academic and industrial laboratories due to its scope, stereospecificity, and mild reaction conditions. The Mitsunobu reaction, like the Wittig, employs a phosphine and produces a phosphine oxide as a byproduct. Like the Wittig reaction, the Mitsunobu reaction often suffers from problems related to product isolation and purification. These issues occur due to the formation of phosphine oxide and hydrazine byproducts.

Figure 8:
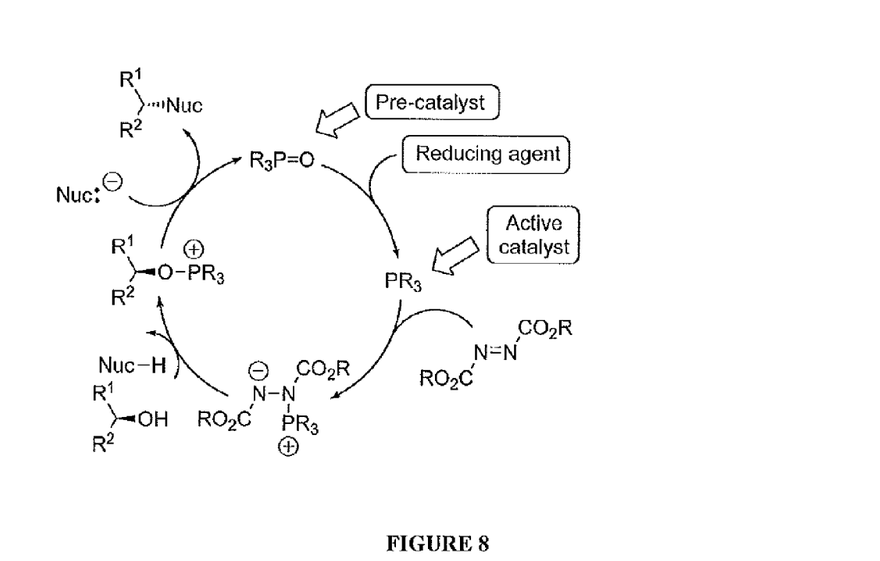
FIG. 8 illustrates the proposed generic catalytic Mitsunobu method.

There are three possible ways the Mitsunobu reaction can be made catalytic: in phosphine, in hydrazine, and in both. FIG. 8 illustrates a Mitsunobu reaction cycle catalytic in phosphine. The most challenging protocol to develop would be the duel catalytic protocol, which would necessitate a reducing agent (phosphine oxide to phosphine) and an oxidizing agent (hydrazine to azo compound) being present in the same flask.

SUMMARY OF THE INVENTION

The invention is directed to a catalytic Wittig method utilizing a phosphine. The method is used to produce an olefin from a reactant and an aldehyde, ketone, or ester. The method includes the steps of providing a phosphine oxide precatalyst and reducing the phosphine oxide precatalyst to produce the phosphine. A phosphonium ylide precursor is then formed from the phosphine and the reactant and then a phosphonium ylide is generated from the phosphonium ylide precursor. This phosphonium ylide is reacted with the aldehyde, ketone, or ester to form the olefin and the phosphine oxide. The phosphine oxide then reenters the cycle.

The method has demonstrated high yields with loadings as low as 4 mol % of a phosphine oxide precatalyst. These yields are comparable to transition metal catalytic protocols. The development of a robust, effective, user friendly, catalytic Wittig protocol will have a profound impact on the synthetic community. Such a process would be widely adopted in academic and industrially laboratories worldwide.

The invention is also directed to a Mitsunobu reaction catalytic in phosphine.

The invention is further directed to a method for recycling a phosphine oxide product produced during a reaction that utilizes a phosphine. The method involves reducing the phosphine oxide to the phosphine.

DETAILED DESCRIPTION OF THE INVENTION

Figure 3:
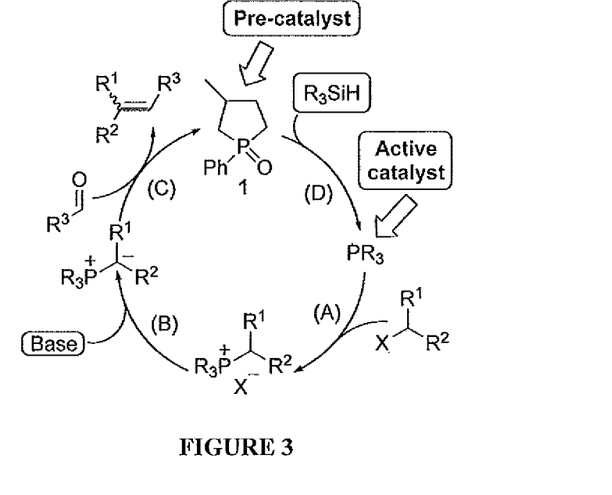
FIG. 3 illustrates the actual catalytic Wittig reaction cycle of the invention.

FIG. 3 shows a schematic of the proposed catalytic Wittig reaction. A indicates the formation of the phosphonium ylide precursor, typically via a phosphonium salt. B indicates the generation of the phosphonium ylide, normally via deprotonation. C indicates the olefination with concomitant generation of phosphine oxide. D indicates the reduction of the phosphine oxide byproduct, producing phosphine to re-enter the catalytic cycle.

Initial studies directed towards a catalytic Wittig reaction were aimed at the systematic evaluation of each step in the proposed catalytic cycle. A phosphine oxide was used rather than a phosphine to remove ambiguity in interpreting the results. The generation of product clearly demonstrates the completion of the steps necessary to achieve a catalytic cycle.

The use of phosphine oxides requires that the first step in the cycle is reduction to the phosphine. As discussed earlier there are few reliable methods to reduce a phosphine oxide; most either use a harsh reducing agent, such as lithium aluminum hydride, or trichlorosilane, either with or without an amine base. Neither of the aforementioned protocols would be compatible with the overall catalytic cycle; lithium aluminum hydride reducing most carbonyl-containing compounds and trichlorosilane reducing the phosphine oxide, normally with inversion. There are reports of retained stereochemistry using the trichlorosilane-amine mixture, but the optical purity is reported as the basis for retention and it is often unreliable. We were not willing to risk inversion, as reduction with loss of stereo-integrity would significantly detract from the realization of a catalytic Wittig protocol with stereo-control. Additionally, the amine base would likely quaternize with the halide wider general reaction conditions. As a general rule the ease of hydride transfer to phosphorus decreases with increased phenyl substitution. It was anticipated that the use of silanes would chemoselectively reduce the phosphine oxide in the presence of an aldehyde or ketone; it was assumed that hydrosilylation would not occur, as this normally requires a transition metal catalyst. In order to ensure a reasonable reduction rate, we employed 3-methyl-1-phenylphospholane-1-oxide rather than triphenylphosphine oxide as the phosphine oxide, because the former is more easily reduced. A further advantage with the employment of 3-methyl-1-phenylphospholane-1-oxide is that its synthesis can be readily achieved as a 2:1 diastereomeric mixture in one step from the commercially available 3-methyl-1-phenyl-2-phospholene-1-oxide under flow hydrogenation conditions.

With the phosphine oxide 3-methyl-1-phenylphospholane-1-oxide in hand we proceeded to evaluate the two key steps in the proposed cycle; namely, D) the reduction of the phosphine oxide to the phosphine and B) the optimization of the base required to effect efficient ylide formation.

The phosphine oxide and reducing silane combination was also used in the Mitsunobu reaction (FIG. 7). We were able to achieve the desired product using the phosphine oxide 3-methyl-1-phenyl-2-phospholene-1-oxide along with phenylsilane as the reducing agent. To the best of our knowledge this is the first example of a Mitsunobu reaction catalytic in phosphine.

Reducing agents can be selected from phenylsilane, diphenylsilane, triphenylsilane, and trimethoxysilane. In principle other reducing agents can be used but they must reduce the phosphine oxide at an acceptable rate and not interfere with the carbonyl starting material or alkene product. Preferably the reducing agent is phenylsilane or diphenylsilane.

Efficient deprotonation to the phosphorus ylide is necessary to effect product formation. Knowing the phosphonium salt has a pKa of approximately 8.5, we set about to evaluate bases. The reduction was attempted in the presence of a mild base in order to mimic potential reaction conditions. Sodium carbonate provided a good yield and complemented the reduction study and was therefore chosen to investigate reaction parameters. Another useful base is sodium tert-butyl carbonate. However, any of a variety of bases could be used. In principle any base can be used as long as it does not interfere with the reducing agent. We were able to achieve reaction using diisopropylethylamine (Hünig's base) and microwave conditions.

Several solvents were evaluated. Toluene proved to be the optimum solvent, while acetonitrile provided good yields but has limited application because of its boiling point. We used toluene in most of our studies but any of a number of solvents could be used such as, for example, 1,2-dichloroethane, cyclopentyl methyl ether, fluorobenzene, 1,4 dioxane, and chlorobenzene.

Figure 10:
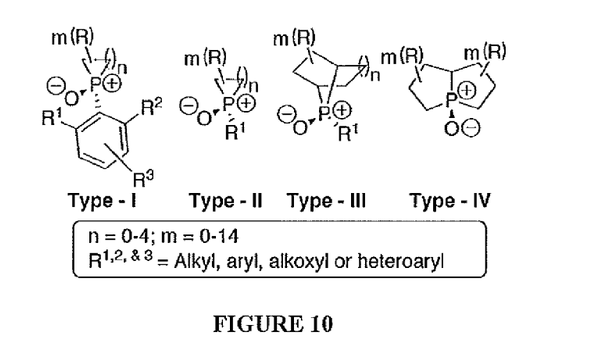
FIG. 10 illustrates proposed phosphine oxide structures.

Although 3-methyl-1-phenyl-2-phospholene-1-oxide is used as the phosphine oxide in the examples, other phosphine oxides could potentially be used in the catalytic Wittig and Mitsunobu methods. Appropriate design of the phosphine can lead to better stereocontrol. A phosphine having a strained cyclic structure is preferable so that its reduction and turnover is possible (cyclic phosphines are easier to reduce due to steric congestion in the transition state). FIG. 10 illustrates some proposed phosphine oxide structures. Rapid entry into phosphine oxides of Type-I can be achieved via methodology detailed by Vedejs and later used by Hoge and Tang and involves the utilization of lithium phosphide anions. Type II oxides are readily available from the corresponding phosphoric acid via conversion to chloride and reaction with a Grignard reagent. Type-III and IV phosphine oxides will be produced as disclosed by Kashman and Mügge respectively. See Krech et al., *Z Anorg. Allg. Chem.* 2003, 629, 1475-1476; and Minge et al., *Organometallics* 2002, 21, 680-684.

Although the invention is described herein as particularly directed to the Wittig and Mitsunobu reactions it should be understood that the invention has broader applicability. The method of the invention can be adapted to be used in any reaction that utilizes a phosphine and produces a phosphine oxide byproduct. The phosphine oxide byproduct can be reduced back to the phosphine and can reenter the reaction cycle. For example, in the Staudinger reaction the combination of an azide with a phosphine or phosphite produces an iminophosphorane intermediate. Combined with the hydrolysis of the aza-ylide to produce a phosphine oxide and an amine, this reaction is a mild method of reducing an azide to an amine. Triphenylphosphine is commonly used as the reducing agent, yielding triphenylphosphine oxide as the side product in addition to the amine.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention, In the examples, unless expressly stated otherwise, amounts and percentages are by weight, temperature is in degrees Celsius or is at ambient temperature, and pressure is at or near atmospheric.

General Experimental

All reagents were purchased from commercial sources and were used without further purification, unless otherwise stated. Dry dimethyl ether (DME) and acetonitrile (ACN) (stored over 4 Å molecular sieves) were purchased from Fluka and handled under argon. Toluene was freshly distilled from calcium hydride and handled under argon. Deuterated solvents were purchased from Cambridge Isotope Laboratories, Inc. Thin layer chromatography (TLC) was performed on Sorbent Technologies Silica G w/UV 254 aluminum-backed plates, and spots were visualized using UV light (254 nm), potassium permanganate, or phosphomolybdic acid stains. Column chromatography purifications were carried out using the flash technique on Sorbent Technologies 60 (230×400 mesh). NMR spectra were recorded on JEOL ECX-300 and JEOL Eclipse+ 500 spectrometers. The chemical shifts (δ) for $^1$H are given in parts per million (ppm) referenced to the residual proton signal of the deuterated solvent (CHCl$_3$ at δ 7.26 ppm); coupling constants are expressed in hertz (Hz). The following abbreviations are used: s=singlet, d=doublet, t=triplet, m=multiplet, dd=doublet of doublets, dt=doublet of triplets, dq=doublet of quartets, q=quartet, and qn=quintet. Gas chromatography was performed on a Varian Series GC/MS/MS 240 System, and the reported yields are based over a calibrated area of undecane as the internal standard. Hydrogenations were performed on an H-Cube Midi™, manufactured by ThalesNano, Hungary. All experiments were conducted under an atmosphere of dry argon unless otherwise noted, using Schlenk technique. Compounds were isolated as mixtures of E and Z, if the reaction was unselective. E and Z refer to the stereochemistry of the bond formed during the reaction.

Synthetic Procedures

Preparation of Compound (I): 3-methyl-1-phenylphospholane-1-oxide. Rapidly, in air, commercially available 3-methyl-1-phenyl-2-phospholene-1-oxide (3.0 g, 16 mmol, CAS 707-61-9) was weighed into a tared 500 mL roundbottom flask. Methanol (300 mL) was added to prepare a 0.05 M solution. The phospholene oxide was hydrogenated via the H-Cube Midi™ with a catalyst cartridge containing 10% Pd/C. The reduction occurred at ambient temperature, under 20 bar $H_2$, at 1 mL/min flow rate. Methanol was removed in vacuo to yield the product as a viscous 2:1 mixture of diastereomers in 100% yield. $^1$H-NMR and $^{31}$P-NMR spectra match previously reported data.

Preparation of Compounds 2-19. The general procedure is outlined at the top of FIG. 6. In air, a 1-dram vial equipped with a stir-bar was charged with 3-methyl-1-phenylphospholane-1-oxide (1) (19 mg, 10 mol %) and base (1.5 mmol, 1.5 equiv.); if the aldehyde was solid, it was added at this point (1.0 mmol, 1.0 equiv.). The vial was then sealed with a septum and purged with argon. Distilled solvent (0.33 mL), silane (1.1-1.5 mmol, 1.1-1.5 equiv.), and organohalide (1.1-1.5 mmol, 1.1-1.5 equiv.) were added; and if the aldehyde was liquid, it was added at this point (1.0 mmol, 1.0 equiv.). The septum was replaced with a PTFE-lined screw cap under an inert atmosphere, and the reaction was heated at 100° C. for 24 h. When GC/MS analysis was not performed, the crude reaction mixture was filtered through a plug of celite, concentrated in vacuo, and purified via flash column chromatography. It is important that the reactions are stirred vigorously in order to achieve maximum yield.

GC/MS Analysis Conditions: Following the General Procedure, n-undecane (GC/MS internal standard, 100 μL/mmol aldehyde) was injected via syringe. The reaction mixture was passed through a short pad of silica gel and analyzed by a GC/MS/MS Varian 240.

Example 1

Phosphine Oxide Reduction Study

This example examined various conditions for reduction of the phosphine oxide 3-methyl-phenylphospholane-1-oxide (1) (Step D in FIG. 3). Diphenylsilane was used for entries 1-11 and 13 and phenylsilane was used for entries 12 and 14. Acetonitrile or toluene was used as the solvent. A base was added to entries 11-14. The reaction was conducted at various temperatures and for various times, as shown in Table 1. Yield was determined by integration of methyl signals in $^1$H NMR.

TABLE 1

| Entry | Silane | Solvent | Base | Temp. (° C.) | Time (min) | Yield (%) |
|---|---|---|---|---|---|---|
| 1 | $Ph_2SiH_2$ | ACN | | 60 | 10 | 11 |
| 2 | $Ph_2SiH_2$ | ACN | | 60 | 20 | 16 |
| 3 | $Ph_2SiH_2$ | ACN | | 60 | 30 | 21 |
| 4 | $Ph_2SiH_2$ | ACN | | 60 | 60 | 25 |
| 5 | $Ph_2SiH_2$ | ACN | | 60 | 120 | 47 |
| 6 | $Ph_2SiH_2$ | ACN | | 70 | 10 | 13 |
| 7 | $Ph_2SiH_2$ | ACN | | 70 | 20 | 24 |
| 8 | $Ph_2SiH_2$ | ACN | | 70 | 30 | 33 |
| 9 | $Ph_2SiH_2$ | ACN | | 70 | 60 | 46 |
| 10 | $Ph_2SiH_2$ | ACN | | 70 | 120 | 70 |
| 11 | $Ph_2SiH_2$ | ACN | 3 equiv $Na_2CO_3$ | 70 | 30 | 10 |
| 12 | $PhSiH_3$ | ACN | 3 equiv $Na_2CO_3$ | 70 | 30 | 6 |
| 13 | $Ph_2SiH_2$ | toluene | 3 equiv $Na_2CO_3$ | 100 | 30 | 69 |
| 14 | $PhSiH_3$ | toluene | 3 equiv $Na_2CO_3$ | 100 | 30 | 74 |

Entries 10 and 13 gave the best yields but toluene was selected as the solvent to use due to concerns with acetonitrile's low boiling point. The presence of the base did impact the results (See Entry 8 vs 11).

Example 2

Second Phosphine Oxide Reduction Study

Figure 4A:
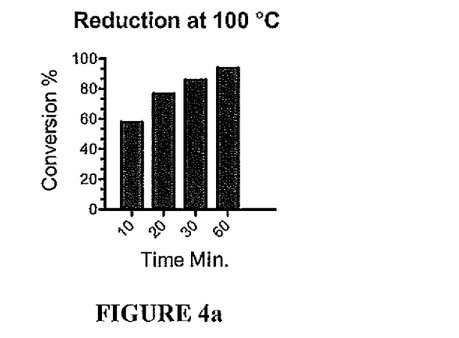
FIGS. 4a and 4b illustrate the results of studies of the reduction of phosphine oxide at 60° C. and 100° C.
Figure 4B:
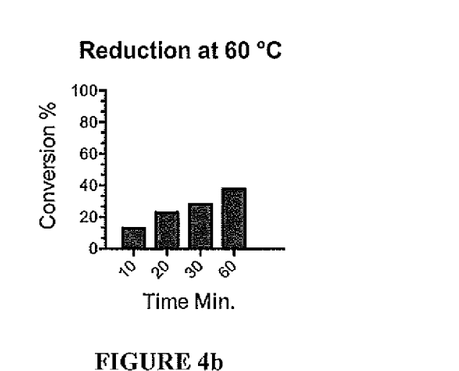

For a viable catalytic Wittig process the phosphine oxide must be reduced/recycled to phosphine at a sufficient rate. If we use palladium catalyzed cross-coupling chemistry as a guide most reactions are complete inside 24 h. If we utilized a catalyst loading of 10 mol % it would need to cycle 10 times to effect a quantitative yield. Assuming the protocol design parameter above the reaction must be complete in 24 h. Thus, the phosphine oxide must be entirely reduced in 2.4 h or less to ensure the protocol design constraint is met. The reduction of the phosphine oxide 1 was tested at 60° C. and 100° C. for times ranging from 10 minutes to one hour. 10 mol % of 1 was used and diphenylsilane was used at 1.2 equivalents. The results, illustrated in FIGS. 4a and 4b, show that a temperature of 100° C. is necessary to maintain an acceptable rate of phosphine oxide reduction.

Example 3

Effects of Base Selection on the Reaction

Example 3 was conducted to evaluate the best base to use for step B-generation of the phosphonium ylide (see FIG. 3). The conditions were similar to Example 4. The reaction was carried out in toluene at 60° C. for 18 h. The base was used at 3 equivalents.

Figure 5:
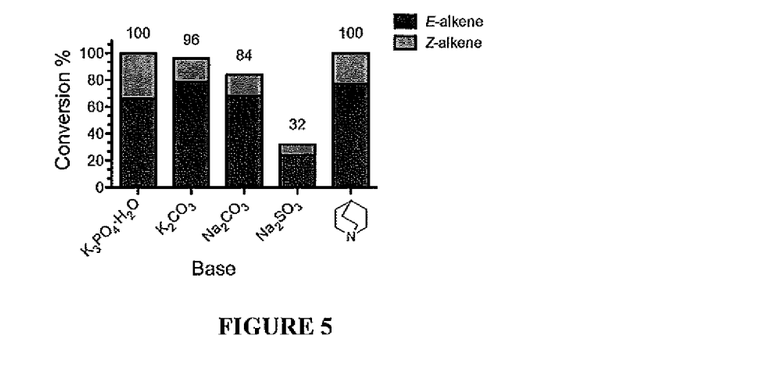
FIG. 5 illustrates the results of a study on the effects of base selection on the reaction.

The results are shown in FIG. 5. Although several bases demonstrated a high yield, sodium carbonate provided a good yield and was selected for further studies due to its inexpensiveness and ease of use.

Example 4

Effects of Silane Choice on the Reaction

The conversion of benzaldehyde to methyl cinnamate (structure 2 in FIG. 6) was attempted with the catalytic process using four different silanes: phenylsilane, diphenylsilane, triphenylsilane, and trimethoxysilane. The results are shown in Table 2. Benzaldehyde was used at 1.0 mmol and methyl bromoacetate at 1.3 mmol. The phosphine oxide (1) was used at 10 mol %. The silane was used at 1.1 mmol and $Na_2CO_3$ was used at 1.5 mmol. The reaction was at 100° C. in toluene. Yields were determined by GC/MS/MS against a calibrated internal standard (undecane) and were performed in duplicate. E/Z ratio was determined by GC/MS/MS. ND means not determined.

TABLE 2

| Entry | Silane | Yield (%) | Ratio (E:Z) |
|---|---|---|---|
| 1 | $Ph_3SiH$ | Trace | ND |
| 2 | $Ph_2SiH_2$ | 75 | 1:0 |
| 3 | $PhSiH_3$ | 46 | 1:0 |
| 4 | $(MeO)_3SiH$ | 61 | 5:2 |

The use of diphenylsilane yielded the desired methyl cinnamate in high yield. Control experiments without phosphine oxide yielded no product (not shown). When the reaction of entry 2 was performed with 4 mol % of the phosphine catalyst, the yield was 73%.

Example 5

Effects of Solvent on the Reaction

Example 5 was conducted to determine the best solvent. The same conditions as Example 4 were used, with variations of the solvent and reaction time as noted in Table 3. Diphenylsilane was used.

TABLE 3

| Entry | Reaction time (hours) | Solvent | Yield (%) | Ratio (E:Z) |
|---|---|---|---|---|
| 1 | 5 | Toluene | 35 | 2.0:1 |
| 2 | 5 | Toluene, wet | 35 | 2.1:1 |
| 3 | 5 | ACN | 42 | 1.6:1 |
| 4 | 5 | DME | 42 | 2.0:1 |
| 5 | 5 | DMF | 34 | 3.4:1 |
| 6 | 5 | 1,4-dioxane | 35 | 2.2:1 |
| 7 | 5 | t-butyl alcohol | 10 | 2.1:1 |
| 8 | 5 | Isopropyl alcohol | 5 | 2.3:1 |
| 9 | 24 | Toluene | 73 | 18:1 |
| 10 | 24 | DME | 56 | 1:0 |
| 11 | 24 | ACN | 85 | 1:0 |
| 12 | 24 | 1,4-dioxane | 55 | 1:0 |

Toluene and acetonitrile provided the best yields at 24 h but acetonitrile has limited application due to its boiling point. Isomeric ratios of approximately 2:1 (E:Z) were consistent among solvents with various dielectric constants.

Example 6

Solvent and Temperature Evaluation

Another evaluation of solvent and temperature was conducted, using the conditions of Example 4, with diphenylsilane. Reaction was for 24 h at the temperatures noted in Table 4. Under these conditions, altering the solvent and temperature produced little variation in yield. However, reducing the temperature to 80° C. (entry 3 vs 4) led to significant amounts of the Z product. This hints at a post-olefination isomerization event, possibly phosphine-mediated. To provide evidence for this hypothesis Z-methyl cinnamate was treated with the phosphine derived from 3-methyl-1-phenylphospholane-1-oxide in $d_6$-benzene at 100° C. (sealed tube). Complete isomerization to the E isomer was observed. The lack of a selective process when trimethoxysilane was employed (Table 2, entry 4) may result from insufficient rate of phosphine formation to effect the complete isomerization of the product after aldehyde consumption.

TABLE 5

| Entry | Solvent | Temp (° C.) | Yield (%) | Ratio (E:Z) |
|---|---|---|---|---|
| 1 | DME | 100 | 50 | 1:0 |
| 2 | CAN | 100 | 52 | 1:0 |
| 3 | Toluene | 100 | 60 | 1:0 |
| 4 | Toluene | 80 | 62 | 2:1 |
| 5 | Toluene | 70 | 49 | 2:1 |
| 6 | Toluene | 60 | 33 | 2:1 |

Example 7

Effects of Pre-Catalyst Loading

We evaluated the effects of precatalyst loading on the yield and E:Z ratio. Similar conditions to Example 4 were used. Diphenylsilane was used at 1.1 equivalents.

TABLE 6

| Entry | Mol % | Yield (%) | Ratio (E:Z) |
|---|---|---|---|
| 1 | 4 | 70 | 1:0 |
| 2 | 10 | 68 | 1:0 |
| 3 | 20 | 80 | 1:0 |

Example 8

Substrate Evaluations

Figure 6:
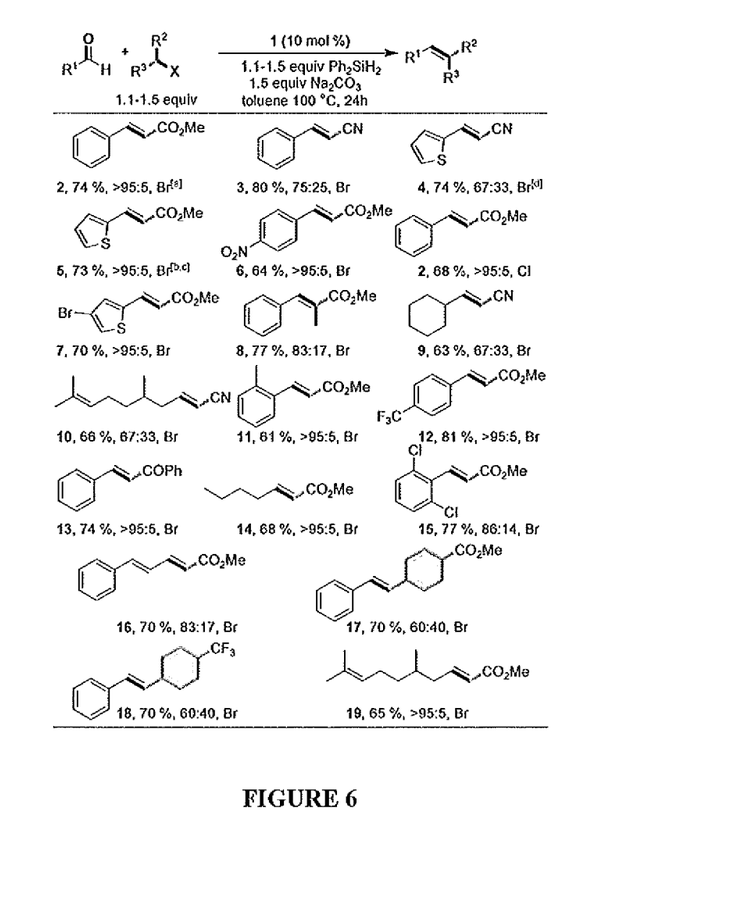
FIG. 6 illustrates the general catalytic reaction in the top section and shows the structures of various products produced according to the catalytic reaction of the invention. For each product the compound number, yield, E/Z ratio, and halide are given.

The following compounds were made using the general catalytic method outlined above. All products were verified via $^1$H-NMR. The structures of each are shown in FIG. 6. The reactions were performed in duplicate.

Notable results were that heterocyclic aldehydes could be employed, with 5 and 7 produced in high yield with diastereocontrol (E/Z); also the synthesis of 10 and 19 from citronellal, and stilbenes 17 and 18 from the corresponding benzyl bromides proceeded in high yields. As anticipated, the use of methyl chloroacetate did not affect the yield (68% versus 74%). Of particular interest is the utilization of a secondary alkyl bromide that yielded a trisubstituted alkene in high yield with moderate E/Z control (product 8). The selectivity of the reaction diminished when benzyl bromides and bromoacetonitrile were utilized (compare products 3 and 18 to 2). In these cases the phosphine isomerization pathway could be significantly reduced or shut down; selectivity would then be governed by the preceding Wittig reaction. The catalytic Wittig protocol was also demonstrated to facilitate the synthesis of practical quantities of alkene, as 5 was produced in 3.39 g, 67% yield with 4 mol % loading of 1. These results permit the development of catalytic phosphine-controlled stereoselective Wittig reactions.

(E)-Methyl cinnamate (2) was obtained from the reaction of benzaldehyde (100 μL, 1.0 mmol, 1.0 equiv.), methyl bromoacetate (114 μL, 1.2 mmol, 1.2 equiv.), diphenylsilane (200 μL, 1.1 mmol, 1.1 equiv.) and sodium carbonate (159 mg, 1.5 mmol, 1.5 equiv.) in toluene (0.33 mL) at 100° C. for 24 h. The crude product was purified via flash column chromatography (benzene/pentane, 50:50, Rf=0.25) to afford the product as a white solid (120 mg, 74%, E:Z 1:0). Spectral data match that of commercially available product (Aldrich). When this reaction was performed with methyl chloroacetate, the isolated yield was 68%.

Cinnamonitrile (3) was obtained from the reaction of benzaldehyde (100 μL, 1.0 mmol, 1.0 equiv.), bromoacetonitrile (73 μL, 1.1 mmol, 1.1 equiv.), diphenylsilane (200 μL, 1.1 mmol, 1.1 equiv.) and sodium carbonate (159 mg, 1.5 mmol, 1.5 equiv.) in toluene (0.33 mL) at 100° C. for 24 h. The crude product was purified via flash column chromatography (benzene/pentane, 30:70, E: Rf=0.11, Z: Rf=0.15) to afford both (E)- and (Z)-3 as colorless oils (103 mg, 80%, E:Z 3:1).

3-(2-Thiophenyl)acrylonitrile (4) was obtained from the reaction of 2-thiophenecarboxaldehyde (94 μL, 1.0 mmol, 1.0 equiv.), bromoacetonitrile (73 μL, 1.1 mmol, 1.1 equiv.), diphenylsilane (200 μL, 1.1 mmol, 1.1 equiv.) and sodium carbonate (159 mg, 1.5 mmol, 1.5 equiv.) in toluene (0.33 mL) at 100° C. for 24 h. The crude product was purified via flash column chromatography (benzene/pentane, 50:50, E: Rf=0.23, Z: Rf=0.23) to afford the isomeric mixture of 4 as a yellow oil (100 mg, 74%, E:Z 2:1). A single reaction employing 2 equiv (MeO)$_3$SiH resulted in 85% yield.

3-(2'-Thiophenyl)-(E)-propenoic acid methyl ester (5) was obtained from the reaction of 2-thiophenecarboxaldehyde (94

µL, 1.0 mmol, 1.0 equiv.), methyl bromoacetate (100 µL, 1.1 mmol, 1.1 equiv.), diphenylsilane (200 µL, 1.1 mmol, 1.1 equiv) and sodium carbonate (159 mg, 1.5 mmol, 1.5 equiv.) in toluene (0.33 mL) at 100° C. for 24 h. The crude product was purified via flash column chromatography (benzene/pentane, 50:50, Rf=0.25) to afford 5 as a light yellow solid (123 mg, 73%, E:Z>95:5). Ester 5[c] was obtained from the reaction of the aldehyde above (1.0 mL, 10.7 mmol, 1.0 equiv.), methyl bromoacetate (1.31 mL, 13.9 mmol, 1.3 equiv.), diphenylsilane (2.37 mL, 12.8 mmol, 1.2 equiv.), sodium carbonate (1.67 g, 16.0 mmol, 1.5 equiv.) and 1 (207 mg, 0.10 mmol, 0.1 equiv.) in toluene (3.6 mL). The reaction was prepared in a 48 mL pressure vessel under an inert atmosphere and run at 100° C. for 24 h to afford the title compound (1.13 g, 63%, E:Z>95:5). Ester 5[d] was obtained from the reaction of the aldehyde above (2.81 mL, 30.0 mmol, 1.0 equiv.), methyl bromoacetate (3.69 mL, 39.0 mmol, 1.3 equiv.), diphenylsilane (6.70 mL, 36.2 mmol, 1.2 equiv.), sodium carbonate (4.75 g, 44.8 mmol, 1.5 equiv.) and 1 (233 mg, 0.04 mmol, 0.04 equiv.) in toluene (3.6 mL). The reaction was prepared in a 75 mL pressure vessel under an inert atmosphere and run at 90° C. for 48 h to afford the title compound (3.39 g, 67%, E:Z>95:5).

3-(4'-Nitrophenyl)-(E)-propenoic acid methyl ester (6) was obtained from the reaction of 4-nitrobenzaldehyde (151 mg, 1.0 mmol, 1.0 equiv.), methyl bromoacetate (100 µL, 1.1 mmol, 1.1 equiv.), diphenylsilane (200 µL, 1.1 mmol, 1.1 equiv.) and sodium carbonate (159 mg, 1.5 mmol, 1.5 equiv.) in toluene (0.33 mL) at 100° C. for 24 h. The crude product was purified via flash column chromatography (EtOAc/pentane, 20:80, Rf=0.32) to afford 6 as a light yellow solid (133 mg, 64%, E:Z>95:5).

3-(4'-bromo-2'-thiophenyl)-(E)-propenoic acid methyl ester (7) was obtained from the reaction of 4-bromothiophene-2 carboxaldehyde (191 mg, 1.0 mmol, 1.0 equiv.), methyl bromoacetate (100 µL, 1.1 mmol, 1.1 equiv.), diphenylsilane (200 µL, 1.1 mmol, 1.1 equiv.) and sodium carbonate (159 mg, 1.5 mmol, 1.5 equiv.) in toluene (0.33 mL) at 100° C. for 24 h. The crude product was purified via flash column chromatography (benzene/pentane, 50:50, Rf=0.20) to afford 7 as a yellow solid (173 mg, 70%, E:Z>95:5).

Methyl 2-methyl-3-phenylacrylate (8) was obtained from the reaction of benzaldehyde (100 µL, 1.0 mmol, 1.0 equiv.), 2-bromopropionic acid methyl ester (145 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 60:40, E: Rf-0.43, Z: Rf-0.43) to afford 8 as a colorless oil (136 mg, 77%, E:Z 5:1).

3-Cyclohexylacrylonitrile (9) was obtained from the reaction of cyclohexanecarboxaldehyde (121 µL, 1.0 mmol, 1.0 equiv.), bromoacetonitrile (91 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (ether/pentane, 1:99, E: Rf=0.09, Z: Rf=0.14) to afford both (E)- and (Z)-9 as a colorless oil (85 mg, 63%, E:Z 2:1).

5,9-Dimethyldeca-2,8-dienenitrile (10) was obtained from the reaction of citronellal (181 µL, 1.0 mmol, 1.0 equiv.), bromoacetonitrile (98 µL, 1.4 mmol, 1.4 equiv.), diphenylsilane (268 µL, 1.5 mmol, 1.5 equiv.) and sodium carbonate (159 mg, 1.5 mmol, 1.5 equiv.) in toluene (0.33 mL) at 100° C. The crude product was purified via flash column chromatography (benzene/pentane, 20:80, E: Rf=0.16, Z: Rf=0.20) to afford both (Z)- and (E)-10 as viscous colorless oils (117 mg, 66%, E:Z 2:1).

(E)-Methyl 3-o-tolylacrylate (11) was obtained from the reaction of 2-methylbenzaldehyde (115 µL, 1.0 mmol, 1.0 equiv.), methyl bromoacetate (125 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 40:60, Rf=0.20) to afford 11 as a colorless oil (107 mg, 61%, E:Z>95:5).

(E)-Methyl 3-(4-(trifluoromethyl)phenyl)acrylate (12) was obtained from the reaction of 4-(trifluoromethyl)benzaldehyde (134 µL, 1.0 mmol, 1.0 equiv.), methyl bromoacetate (125 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 35:65, Rf=0.22) to afford 12 as a white solid (186 mg, 81%, E:Z>95:5).

Chalcone (13) was obtained from the reaction of benzaldehyde (100 µL, 1.0 mmol, 1.0 equiv.), 2-bromoacetophenone (299 mg, 1.5 mmol, 1.5 equiv.), diphenylsilane (190 µL, 1.1 mmol, 1.1 equiv.) and sodium bicarbonate (126 mg, 1.5 mmol, 1.5 equiv.) in toluene (0.33 mL) at 100° C. for 24 h. The crude product was purified via flash column chromatography (benzene/pentane, 35:65, Rf=0.21) to afford 13 as a light yellow solid (154 mg, 74%, E:Z>95:5).

(E)-Methyl hept-2-enoate (14) was obtained from the reaction of valeraldehyde (106 µL, 1.0 mmol, 1.0 equiv.), methyl bromoacetate (125 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 66:33, Rf=0.30) to afford 14 as a colorless oil (97 mg, 68%, E:Z>95:5).

Methyl 2,6-dichlorocinnamate (15) was obtained from the reaction of 2,6-dichlorobenzaldehyde (175 mg, 1.0 mmol, 1.0 equiv.), methyl bromoacetate (125 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 35:65, E: Rf=0.26, Z: Rf=0.26) to afford an isomeric mixture of 15 as a viscous colorless oil (178 mg, 77%, E:Z 6:1).

5-Phenyl-2,4-pentadienoic acid methyl ester (16) was obtained from the reaction of cinnamaldehyde (126 µL, 1.0 mmol, 1.0 equiv.), methyl bromoacetate (125 µL, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 50:50, E: Rf=0.23, Z: Rf=0.36) to afford E and Z isomers of 16 as a white solid and a colorless oil, respectively (132 mg, 70%, E:Z 5:1). The minor diastereomer was assigned based on the different coupling constants and the spectrum of the known isomer.

Methyl 4-styrylbenzoate (17) was obtained from the reaction of benzaldehyde (100 µL, 1.0 mmol, 1.0 equiv.), 4-(bromomethyl)benzoic acid methyl ester (298 mg, 1.3 mmol, 1.3 equiv.), diphenylsilane (225 µL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 35:65, E: Rf=0.37, Z: Rf=0.51) to afford (E)-17 as a white solid and (Z)-17 as a viscous colorless oil (167 mg, 70%, E:Z 3:2).

1-(4-Trifluoromethylphenyl)-2-phenylethylene (18) was obtained from the reaction of benzaldehyde (100 μL, 1.0 mmol, 1.0 equiv.), 4-(trifluoromethyl)benzyl bromide (232 μL, 1.5 mmol, 1.5 equiv.), diphenylsilane (230 μL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (pentane, 100:0, E: Rf=0.42, Z: Rf=0.55) to afford (E)-18 as a white solid and (Z)-18 as a colorless oil (174 mg, 70%, E:Z 3:2).

(E)-Methyl 5,9-dimethyldeca-2,8-dienoate (19) was obtained from the reaction of citronellal (180 μL, 1.0 mmol, 1.0 equiv.), methyl bromoacetate (125 μL, 1.3 mmol, 1.3 equiv.), diphenylsilane (225 μL, 1.2 mmol, 1.2 equiv.) and sodium carbonate (159 mg, 1.5 mmol, 1.5 equiv.) in toluene (0.33 mL) at 100° C. for 24 h. The crude product was purified via flash column chromatography (benzene/pentane, 30:70, Rf=0.17) to afford 19 as a colorless oil (137 mg, 65%, E:Z>95:5).

Example 9

Evaluation of the Mechanism for the Formation of the E-Selective Wittig Product

The reaction is E-selective in toluene at 85° C., 90° C. and 100° C. over 24 hours. We believe this occurs via Michael addition of the phosphine to the Z-isomer. This mechanism was evaluated using 20 mol % phosphine oxide (1) with isomerically pure Z-methyl cinnamate at 80° C. for 24 hours. Proton NMR supports this mechanistic pathway.

Example 10

The Catalytic Mitsunobu Method to Synthesize Benzyl 4-Nitrobenzoate

Figure 9:
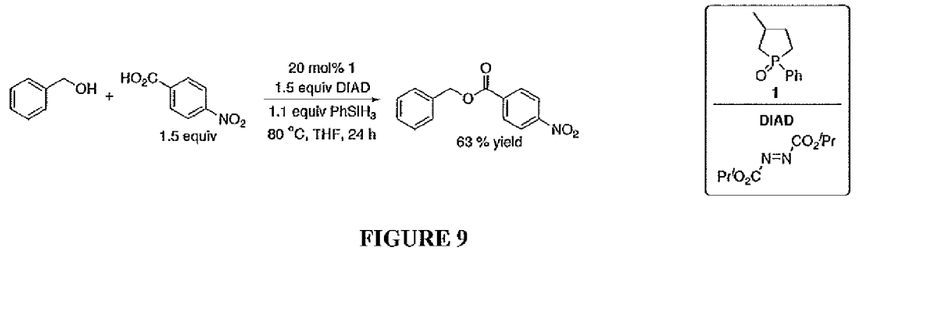
FIG. 9 illustrates a catalytic Mitsunobu reaction.

The reaction is illustrated in FIG. 9. In air, a 1-dram vial equipped with a stir-bar was charged with phosphine oxide 1 (9.7 mg, 10 mol %), 4-nitrobenzoic acid (51.7 μL, 0.5 mmol), and diisopropyl azodicarboxylate (DIAD, 147.5 μL, 0.75 mmol). The vial was then sealed with a septum, and purged with argon. Distilled Toluene (1.5 mL) was added. Reaction was allowed to stir. Phenylsilane (67.8 μL, 0.55 mmol), and benzyl alcohol (51.7 μL, 0.5 mmol) was added. The septum was replaced with a PTFE-lined screw cap under an inert atmosphere, and the reaction was heated at 80° C. for 24 hours. The crude reaction mixture was filtered through a plug of celite, concentrated in vacuo, and purified via flash chromatography yielding the title compound 63%, 81.0 mg. To the best of our knowledge this is the first example of a Mitsunobu reaction catalytic in phosphine.

Example 11

Synthesis of Stilbene

In air, a 1-dram vial equipped with a stir-bar was charged with phosphine oxide 1 (19 mg, 10 mol %), and sodium tert-butyl carbonate (1.5 mmol, 1.5 equiv.) The vial was then sealed with a septum and purged with argon. Distilled toluene (1.00 mL), diphenylsilane (1.2 mmol, 1.2 equiv.), and benzyl bromide (1.2 mmol, 1.2 equiv.) was added. Benzaldehyde (1.0 mmol, 1.0 equiv.) was added slowly via syringe over five hours. The reaction was heated at 100° C. for 20 h. The yield of stilbene was determined to be (cis) 28.86% and (trans) 54.05% for a combined yield of 82.91%. $^1$H-NMR spectra match that of the commercially available compounds, cis-stilbene (Alfa Aesar), and trans-stilbene (TCI).

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A one-pot catalytic Wittig method to form an olefin from an organohalide and an aldehyde or ketone comprising the steps:
    a) providing i) the organohalide, ii) the aldehyde or ketone, iii) a phosphine oxide, and iv) a silane reducing agent;
    b) reducing the phosphine oxide with the silane reducing agent to produce a phosphine;
    c) forming a phosphonium ylide precursor with the phosphine and organohalide;
    d) generating a phosphonium ylide from the phosphonium ylide precursor; and
    e) reacting the phosphonium ylide with the aldehyde or ketone to form the olefin and said phosphine oxide; wherein the phosphine oxide is selected from the group:

wherein n is between 0 and 4; m is between 0 and 14; and R is an alkyl; $R^1$, $R^2$, and $R^3$ are each an alkyl, aryl, alkoxy, or heteroaryl; and the organohalide is a primary or secondary organohalide.

2. The catalytic Wittig method of claim 1, wherein the phosphonium ylide precursor is a phosphonium salt.

3. The catalytic Wittig method of claim 1, wherein the phosphonium ylide is generated via deprotonation.

4. The catalytic Wittig method of claim 1, wherein the reducing agent is selected from the group consisting of phenylsilane, diphenylsilane, triphenylsilane, and trimethoxysilane.

5. The catalytic Wittig method of claim 1, wherein the reducing agent is selected from the group consisting of phenylsilane and diphenylsilane.

6. The catalytic Wittig method of claim 1, wherein step d is performed in the presence of a base selected from the group $Na_2CO_3$, Hunigs base (N,N-diisopropylethylamine), and sodium tert-butyl carbonate.

7. The catalytic Wittig method of claim 1, wherein the phosphine oxide is 3-methyl-1-phenylphospholane-1-oxide.

8. The catalytic Wittig method of claim 1, wherein the conditions are selected to selectively achieve the E or Z isomer.

9. The catalytic Wittig method of claim 1, wherein the phosphine oxide is generated from a phosphine species.

10. The method of claim 1, wherein the phosphine oxide is selected from the group:

wherein n is 3; m is 0; $R^1$, $R^2$, and $R^3$ are each an alkyl, aryl, alkoxy, or heteroaryl; and the reducing agent is a silane selected from the group phenylsilane, diphenylsilane, triphenylsilane, and trimethoxysilane.

11. The method of claim 1 wherein the phosphine oxide is selected from the group:

wherein n is 3; m is 0; $R^1$, $R^2$, and $R^3$ are each an alkyl, aryl, or alkoxy; and the reducing agent is a silane selected from the group phenylsilane, diphenylsilane, triphenylsilane, and trimethoxysilane.

12. The method of claim 1 wherein, the phosphine oxide is selected from the group:

wherein n is 3; m is 0; $R^1$, $R^2$, and $R^3$ are each an alkyl or aryl; and the reducing agent is a silane selected from the group phenylsilane, diphenylsilane, triphenylsilane, and trimethoxysilane.

13. The method of claim 1 wherein, the phosphine oxide has the formula:

wherein n is 0 to 4; m is 0; and $R^1$ is alkyl, aryl, alkoxy, or heteroaryl.

14. The method of claim 1, wherein the organohalide is selected from the group methyl bromoacetate, bromoacetonitrile, 2-bromopropionic acid methyl ester, 2-bromoacetphenone, benzyl bromide, and trifluoromethyl benzyl bromide.

15. A method for the chemoselective reduction of a phosphine oxide to a phosphine in the presence of an organohalide, an aldehyde or a ketone, and an alkene; wherein said phosphine oxide is reduced using a silane reducing agent.

16. The method of claim 15, wherein the organosilane is selected from the group phenylsilane, diphenylsilane, triphenylsilane, and trimethoxysilane.

17. The method of claim 15, wherein the phosphine oxide is a cyclic phosphine oxide.

18. The method of claim 15, wherein the organosilane is selected from the group phenylsilane, diphenylsilane, triphenylsilane, and trimethoxysilane; and the phosphine oxide is a cyclic phosphine oxide.

19. The method of claim 15, wherein the organosilane is selected from the group phenylsilane, diphenylsilane, triphenylsilane, and trimethoxysilane; and the phosphine oxide is 3-methyl-1-phenylphospholane-1-oxide.

20. The method of claim 15, wherein the phosphine oxide is selected from the group:

wherein n is 0 to 4; m is 0 to 14; R is an alkyl; and $R^1$, $R^2$, and $R^3$ are each an alkyl, aryl, alkoxy, or heteroaryl.

21. The method of claim 15, wherein the phosphine oxide is selected from the group:

wherein n is 0 to 4; m is 0; and $R^1$, $R^2$, and $R^3$ are each an alkyl, aryl, alkoxy, or heteroaryl.

22. The method of claim 15, wherein the phosphine oxide is selected from the group wherein n is 0 to 4; m is 0; $R^1$, $R^2$, and $R^3$ are each an alkyl, aryl, alkoxy, or heteroaryl; and the silane is selected from the group phenylsilane, diphenylsilane, triphenylsilane, and trimethoxysilane.

23. The method of claim 15, wherein the phosphine oxide is 3-methyl-1-phenylphospholane-1-oxide.

* * * * *